United States Patent [19]
Harrison et al.

[11] Patent Number: 5,366,728
[45] Date of Patent: * Nov. 22, 1994

[54] **STABLE FORMS OF ANTIGENIC *TAENIA OVIS* POLYPEPTIDES**

[75] Inventors: Gavin B. L. Harrison; Robert P. Dempster, both of Upper Hutt, New Zealand; Michael D. Rickard, Werribee; Marshall W. Lightowlers, Victoria, both of Australia; David D. Heath, Paremata; Stephen B. Lawrence, Upper Hutt, both of New Zealand; Kim L. O'Hoy, Pascoe Vale, Australia

[73] Assignees: Pitman-Moore New Zealand Limited, Upper Hutt, New Zealand; The University of Melbourne, Melbourne, Australia; Her Majesty the Queen in right of New Zealand through the Ministry of Agriculture & Fisheries, Wellington, New Zealand

[ * ] Notice: The portion of the term of this patent subsequent to Mar. 9, 2010 has been disclaimed.

[21] Appl. No.: 969,450

[22] Filed: Oct. 30, 1992

Related U.S. Application Data

[63] Continuation of Ser. No. 818,453, Jan. 3, 1992, Pat. No. 5,192,538, which is a continuation of Ser. No. 470,691, Jan. 26, 1990, abandoned, which is a continuation-in-part of Ser. No. 349,723, May 9, 1989.

[30] Foreign Application Priority Data

Jan. 6, 1988 [NZ] New Zealand .......................... 24862
Dec. 5, 1988 [NZ] New Zealand ......................... 224597

[51] Int. Cl.$^5$ ..................... A61K 39/00; C12N 15/12; C07K 9/00; C07K 15/08
[52] U.S. Cl. .................................. 424/191.1; 514/2; 514/8; 514/12; 530/350; 530/395; 530/806; 530/855; 435/69.3; 435/252.3; 435/252.33; 435/320.1; 536/23.1; 536/23.4; 424/266.1
[58] Field of Search .................. 424/88; 514/2, 8, 12; 435/69.3, 320.1, 252.3, 252.33; 530/350, 395; 536/23.1, 23.4

[56] References Cited

U.S. PATENT DOCUMENTS 5,192,538 3/1993 Harrison et al. ..................... 424/88

FOREIGN PATENT DOCUMENTS 2219590 12/1989 United Kingdom ........ C12N 15/00
2232675 12/1990 United Kingdom ........ C12N 15/12

OTHER PUBLICATIONS

Howell, M. J. et al. "Cloning and expression of *Taenia ovis* antigens . . . ", Mol. & Biochemical Parasitology 28 (1988), pp. 21–30.
Johnson, K. S. et al. "Vaccination against ovine cysticerosis . . . " Nature, vol. 338, 13 Apr. 1989, pp. 585–587.
Bowtell, D. D. L., et al., Parasitology 93:599–610 (1986), "Immunochemical analysis of *Taenia taeniaeformis* antigens expressed in *Escherichia coli*,".
Cougle W. G., et al., Mol. and Biochem. Parasitol. 45:137–146 (1991), "Molecular cloning of *Taenia taeniaeformis* onocosphere antigen genes".
Heath, D. D., et al., J. Parasitol 71(2):192–199 (1985), "The use of excretory y antigens of the scolex of *Tenia ovis* for the serodiagnosis of infection in dogs".

(List continued on next page.)

Primary Examiner—Christine M. Nucker
Assistant Examiner—T. Cunningham
Attorney, Agent, or Firm—Nixon & Vanderhye

[57] ABSTRACT

Stable forms of *Taenia ovis* peptide antigens, such as portions of a *T. ovis* oncosphere antigen which runs as a 47–52 kDa doublet, are suitable for use in vaccines to protect ruminants against infection by cestode parasites. The antigens are preferably obtained by isolation and expression of the DNA encoding them in recombinant host cells. Aspects of the invention include DNA encoding *T. ovis* antigens, vectors containing such DNA and host cells which express the *T. ovis* antigens.

27 Claims, 4 Drawing Sheets

OTHER PUBLICATIONS

Howell, M. J., et al., Mol. and Biochem. Parasitol. 28:21–30 (1988), "Cloning and expression of *Taenia ovis* antigens in *Escherichia coli*".

Howell, M. J., et al., Int. J. for Parasitol. 19(6):631–638 (1989), "Characterization of cloned antigens of *Taenia ovis*".

Johnson, K. S., et al., Nature 338:585–587 (13 Apr. 1989), "Vaccination against ovine cysticerosis using a defined recombinant antigen".

Osborn, P. J., et al., Res. in Veterin. Sci. 32:351–353 (1982), "Vaccination of sheep against *Taenia ovis*. The response to various dose rates of antigens obtained by incubation of oncosphered *in vitro*,".

Rickard, M. D., et al., Parasitology 75:183–188 (1977), "Vaccination of lambs against infection with *Taenia ovis* using antigens collected furing short-term *in vitro* incubation of activated *T. ovis* oncospheres".

Rickard, M. D., et al., Australian Veterin. J. 52:209–215 (1976), "Vaccination of lambs against infection with *Taenia ovis*".

| | | | | | | | | | | | | | |
|---|---|---|---|---|---|---|---|---|---|---|---|---|---|
| 1 | | CG | GAC | TAC | GAA | CAA | CCC | ATC | GAG | AGA | ACA | GTG | GTA | GAA |
| | | | Asp | Tyr | Glu | Gln | Pro | Ile | Glu | Arg | Thr | Val | Val | Glu | 12 |

```
  1       CG GAC TAC GAA CAA CCC ATC GAG AGA ACA GTG GTA GAA
             Asp Tyr Glu Gln Pro Ile Glu Arg Thr Val Val Glu   12

39  TAT CCA TCA CTA CGT GAC ATC TTT GCT TGG GAA CCT CCG ACT TCT
     Tyr Pro Ser Leu Arg Asp Ile Phe Ala Trp Glu Pro Pro Thr Ser   27

84  AAC TCC ATT GGC CTA ACT TGG CAA AGG CAT GCA TTT CCT GGT GTG
     Asn Ser Ile Gly Leu Thr Trp Gln Arg His Ala Phe Pro Gly Val   42

129  GAA CGT GAA GTG CTC ACA TTG AAG GCA GTG CCG ACT TCT GAA CCC
     Glu Arg Glu Val Leu Thr Leu Lys Ala Val Pro Thr Ser Glu Pro   57

174  AAT AAC ACC AAG ACA GCA TAT GCA AAG CTC GGC AGC GGA AAA GTC
     Asn Asn Thr Lys Thr Ala Tyr Ala Lys Leu Gly Ser Gly Lys Val   72

219  ACT CTT GAT GGA CTG AAG CCC AAT GCC ACA TAT CTT GTG ACT GCG
     Thr Leu Asp Gly Leu Lys Pro Asn Ala Thr Tyr Leu Val Thr Ala   87

264  ACG GCA AAT ATA AGT GGA GAC ACA ATT CTG GTA TTG AGC AAT ACT
     Thr Ala Asn Ile Ser Gly Asp Thr Ile Leu Val Leu Ser Asn Thr  102

309  TTT CAT ACA CTG GCC AAT GGC ACA AAT ATT ATA AAT AAC ATC TTC
     Phe His Thr Leu Ala Asn Gly Thr Asn Ile Ile Asn Asn Ile Phe  117

354  CAT TGG GGT CCT GTG ACT AAT CAA TCA ATT CAA GTA AGA TGG GAT
     His Trp Gly Pro Val Thr Asn Gln Ser Ile Gln Val Arg Trp Asp  132

399  CAG ATA AAA CCG GAG GAA ACA AGC GCT CTG ATA GTC ACA CTG ACG
     Gln Ile Lys Pro Glu Glu Thr Ser Ala Leu Ile Val Thr Leu Thr  147

444  GCA GAG ATG GCT TCT GAC CCC GGA GTG GAA AGA TCG GAG TCT GCA
     Ala Glu Met Ala Ser Asp Pro Gly Val Glu Arg Ser Glu Ser Ala  162

489  CTC TTC GGT AAA GGA AAG GTC ACT GTT GAC GGA CTG GAG TCC GAC
     Leu Phe Gly Lys Gly Lys Val Thr Val Asp Gly Leu Glu Ser Asp  177

534  ACA CTA TAT ATT GCG ACT GTG ATG GTA TTT AGA AAT GGA AGG CAA
     Thr Leu Try Ile Ala Thr Val Met Val Phe Arg Asn Gly Asg Gln  192

579  TAC TTC AAT TCC ACC AGA GAT ATT CGA ACA CTC AAA TCT GGC CAT
     Thr Phe Asn Ser Thr Arg Asp Ile Arg Thr Leu Lys Ser Gly His  207

624  AAG GAG GTA ACA GTC GTA ACA ACT AGT GGA TC
     Lys Glu Val Thr Val Val Thr Thr Ser Gly
```

*Figure 1*

Autoradiograph of GST fusion proteins reacted with the monoclonal antibody 3F10F6

LANE 1 : GST 45W (BamHI/HincII)

LANE 2 : GST 45W (BamHI/XhoII)

LANE 3 : GST - 45W

LANE 4 : GST - 45S

LANE 5 : GST

Figure 3

― 52
― 47 kDa 1 2 3 4 5 6 7 8 9

T. ovis oncosphere antigen extract probed with sera from sheep injected with:

LANE 1: Saline Control

LANE 2,3: GST 45W affinity purified

LANE 4,5: GST 45W (B/X) affinity purified

LANE 6,7: GST 45W (B/X) urea extract

LANE 8,9: GST 45W (B/X) urea extract/affinity purified

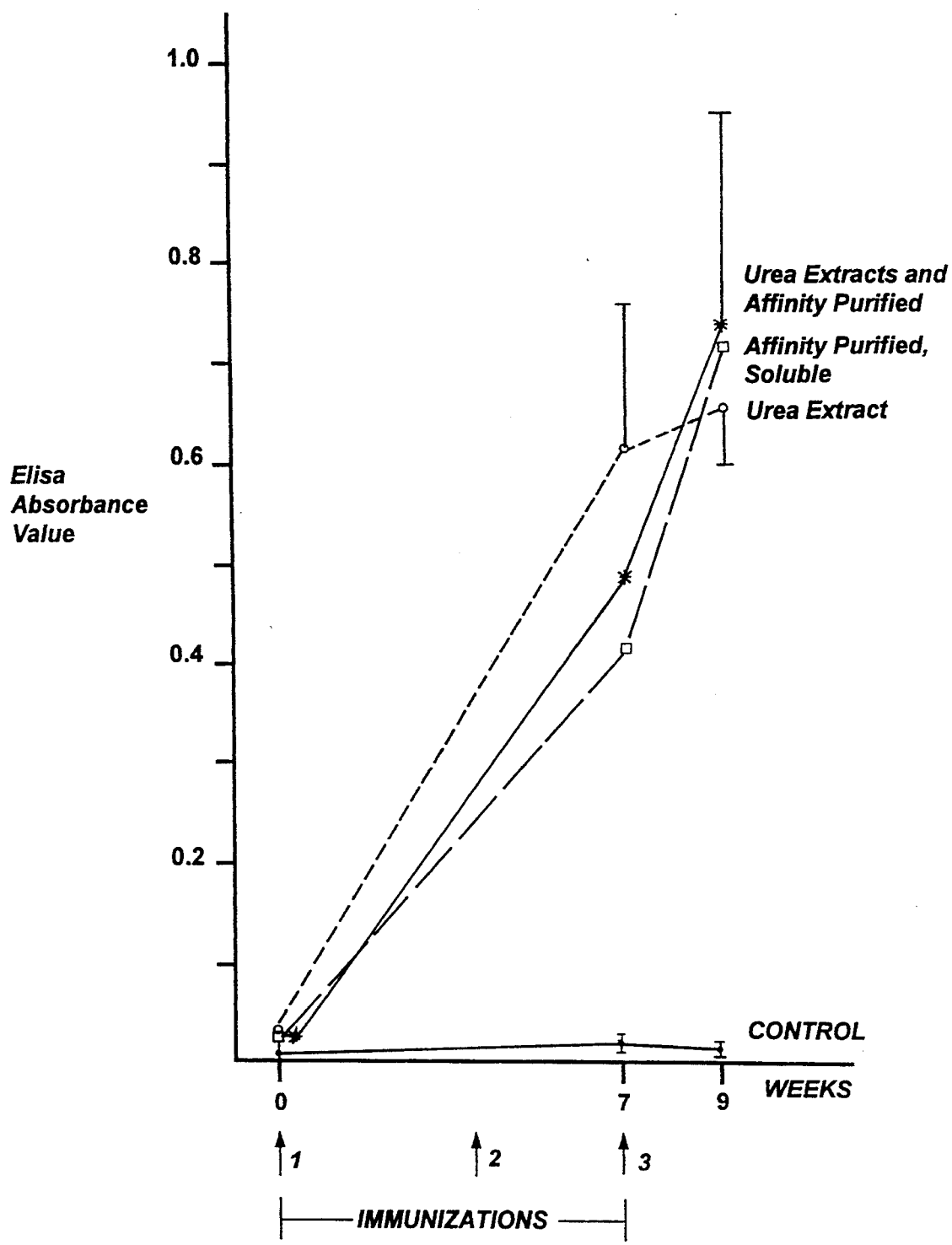
Figure 4. Sheep antibody response following immunization with fusion protein extracts

STABLE FORMS OF ANTIGENIC *TAENIA OVIS* POLYPEPTIDES

This is a continuation of application Ser. No. 07/818,453, filed Jan. 3, 1992, now U.S. Pat. No. 5,192,538, which is a continuation of U.S. Ser. No. 07/470,691, filed Jan. 26, 1990, now abandoned, which is a continuation-in-part of U.S. Ser. No. 07/349,723, filed May 9, 1989.

This invention relates to stable forms of peptide antigens of T.ovis suitable for use in vaccines to protect ruminants against infection by cestode parasites. The antigens are preferably obtained by expression of DNA coding therefor in a recombinant host cell. Aspects of the invention include DNA encoding the antigens, vectors containing the DNA and hosts which express the antigens.

BACKGROUND OF THE INVENTION

The *Taenia ovis* tapeworm exists in adult form in the small intestine of its primary host, the dog. The cystic stage is carried in the musculature of its secondary or intermediate hosts, notably sheep and goats. Current control measures include prevention of feeding of infected carcases to dogs and treatment of dogs with cestocidal drugs, notably praziquantel (Droncit, Bayer) to prevent transmission of the parasite to ruminants. These control measures are costly to implement and are not effective in eradicating *T.ovis*.

Accordingly, as an adjunct to current control measures and to effect eradication of the disease, it would be preferable to immunise the secondary hosts to protect them from infection and also to preserve carcase quality for the meat industry.

Previous investigations conducted into vaccination against *T.ovis* infection with oncosphere antigens are reviewed by Rickard, M. D. and Williams, J. F, Hydatidosis/Cystercercosis: Immune mechanisms and Immunisation against infection, *Adv Parasitology* 21, 230–296 (1982). However, in the work reviewed no attempt was made to identify which antigenic component of the oncospheres was responsible for the immune response. As will be appreciated, T.ovis contains a large number of antigenic components, most of which are not immunologically effective against infection.

Earlier attempts have been made to identify a host protective antigen for *T.ovis* (Howell, M. J & Hargreaves, J J *Mol Biochem Parasitol* 28, 21–30 (1988)). A cDNA library was prepared using mRNA extracted from adult *T. ovis* tape worms. Recombinants expressing antigenic determinants as β-galactosidase fusion proteins were selected using antibodies in serum from sheep infected with *T. ovis*. Some fusion proteins were shown to correspond with native antigens (92.5 to 180 kD) present in adult and oncosphere stages of *T.ovis*, but trials of the host-protective nature of purified fusion proteins were not reported.

In Johnson, K. S. et al, Nature 338, 585–587 (1989), the present inventors have described the identification and cloning of a native polypeptide of *T.ovis* capable of generating a protective immunological response in ruminants against *T.ovis* infection. However, the recombinant polypeptide described in this paper has been found to be less stable than is optimal for the production of a commercial vaccine.

It is accordingly an object of the present invention to provide a stable form of protective antigen for use in vaccines for the protection of ruminants against *T.ovis* infection or at least to provide the public with a useful choice.

SUMMARY OF INVENTION

Accordingly, in one aspect the present invention may broadly be said to consist in a purified stable antigenic peptide comprising a fragment of a *T.ovis* polypeptide, which fragment (a) has a molecular weight of from about 23 kD to about 24 kD; and (b) is capable of generating a protective immunological response to *T.ovis* in a ruminant or a subfragment or variant thereof having substantially equivalent stability and immunological activity thereto.

Preferably, the antigenic polypeptide fragment has the amino acid sequence set out in FIG. 1.

Conveniently, the protective antigenic peptide of the invention is obtained by expression of the DNA sequence coding therefor in a host cell or organism.

In a further aspect, the invention consists in a stable antigenic peptide comprising a fragment of a *T.ovis* polypeptide which is capable of generating a protective immunological response to *T.ovis* in a ruminant, which fragment has the amino acid sequence encoded by the DNA sequence of FIG. 1 herein, or a derivative or variant thereof having substantially equivalent stability and immunological activity thereto.

In still a further aspect, the invention consists in a composition of matter capable of generating a protective immunological response to T.ovis infection in a ruminant which essentially consists of:

(a) a stable peptide comprising a polypeptide fragment having the amino acid sequence of FIG. 1;

(b) a stable immunologically active subfragment of (a); or (c) a variant of (a) or (b) which has been modified by the insertion, substitution or deletion of one or more amino acids and which has equivalent stability and immunological activity thereto.

In still a further aspect, the invention consists in a vaccine which includes a stable immunogenic peptide thereof as defined above in combination with a pharmaceutically acceptable carrier and/or adjuvant therefor.

In still a further aspect, the invention may be said to consist in a method of protecting a ruminant against infection by a cestode parasite comprising administering to said ruminant an immunologically effective amount of:

(a) a stable peptide as defined above;

(b) a composition as defined above; or (c) a vaccine as defined above.

In additional aspects, the invention relates to a DNA isolate which comprises a DNA sequence encoding the immunologically effective antigenic peptide of the invention; to transformed hosts capable of expressing the antigenic peptide encoded; and to methods of producing the antigenic peptide comprising culturing the said transformed hosts.

BRIEF DESCRIPTION OF THE DRAWINGS

Although the invention is broadly as described above, it will be appreciated by those persons skilled in the art that the invention is not limited to the foregoing but also includes embodiments of which the following gives examples. In particular, certain aspects of the invention will be more clearly understood by having reference to the accompanying drawings wherein, FIG. 1 represents both the nucleotide sequence and the predicted amino acid sequence of the T. ovis polypeptide fragment.

FIG. 3 is an immunoblot analysis showing that sheep vaccinated with the cloned GST 45W (B/X) peptide generate antibodies which recognise the native T. ovis antigen(s) having a molecular weight of 47-52 kD.

FIG. 4 shows sheep antibody response following immunisation with GST-45W (B/X) fusion protein extracts.

DETAILED DESCRIPTION OF THE INVENTION

Figure 2:
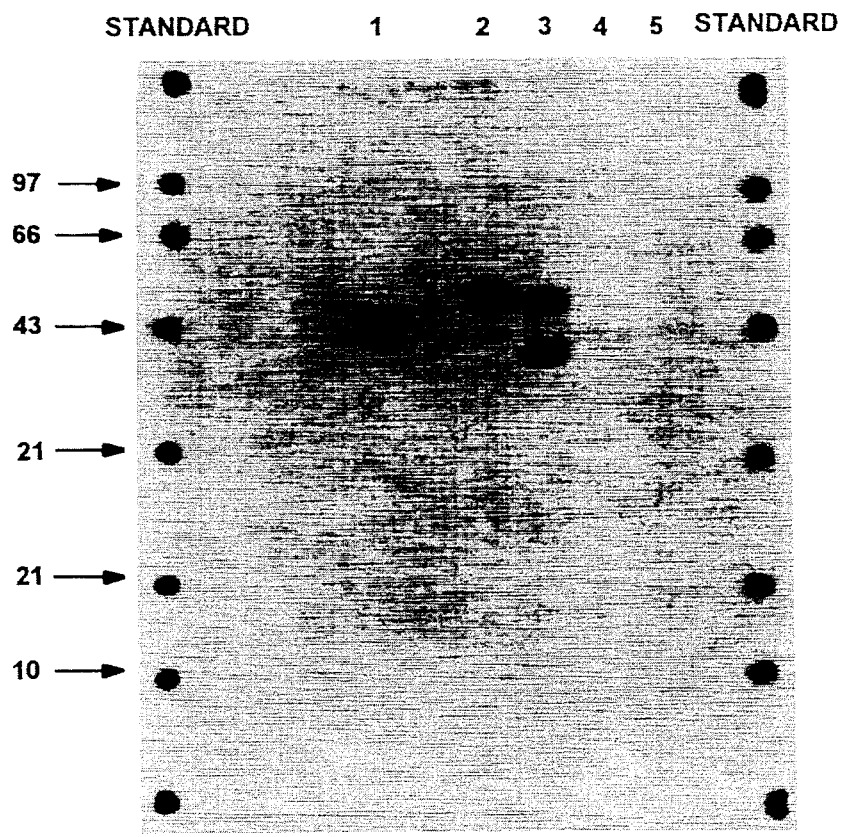
FIG. 2 is an autoradiograph showing that a monoclonal antibody generated against GST-45W fusion protein recognises the cloned B-X peptide of the invention.

Previous investigations by the inventors have identified a 47-52 kD molecular weight fraction of the antigenic complement of T. ovis as a major antigen to which antibodies were present in immune sheep. The cloning and recombinant production of this native antigen in general and of a major fragment of the antigen in particular (termed the "45 W" antigen) has been reported (Johnson, K. S. et al, Nature (1989), supra), and forms the subject of U.S. Ser. No. 07/349,723, the disclosure of which is specifically incorporated herein by reference However, during the course of subsequent investigations into the production of a commercial vaccine based upon this major fragment it was found that although it was perfectly possible to produce a vaccine composition protective against T. ovis, the stability of the fragment itself was less than ideal.

In further investigations, the inventors have now located a subfragment of the 45 W antigen which exhibits enhanced stability while also having equivalent if not superior immunological activity as compared to the 45 W antigen. It is to this more stable subfragment that the present invention is primarily directed.

The present invention therefore has as its first aspect an antigenic peptide comprising a fragment of a T.ovis polypeptide which is capable of generating a protective immunological response to T.ovis. The molecular weight of this fragment has been calculated as about 20 kD from the DNA sequence determined for the molecule.

In a preferred form of this aspect of the invention, the immunologically active peptide includes a polypeptide fragment having the amino acid sequence of FIG. 1. It will however be appreciated that modifications can be made to the native sequence of the polypeptide fragment whilst at least substantially retaining both its stability and biological activity. Such modifications to the native amino acid sequence to result in the insertion, substitution or deletion of one or more amino acids are specifically within the scope of this invention.

The antigenic polypeptide fragments of the invention can be prepared in a variety of ways. For example, they can be obtained by isolation from a natural source, by synthesis using any suitable known technique (such as by the stepwise solid phase approach described by Merrifield (1963) J. Amer Chem. Soc 85 2149-2156) or, as is preferred, through employing recombinant DNA techniques.

The variants of the polypeptide fragments can similarly be made by any of those techniques known in the art. For example, variants can be prepared by site-specific mutagenesis of the DNA encoding the native amino acid sequence.

Site-specific mutagenesis allows the production of variants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., DNA 2, 183 (1983).

In a further aspect, the invention accordingly relates to the recombinant production of the stable antigenic peptide defined above.

Stated generally, the production of the protective antigen of the invention by recombinant DNA techniques involves the transformation of a suitable host organism or cell with an expression vector including a DNA sequence coding for the antigen, followed by the culturing of the transformed host and subsequent recovery of the antigen expressed.

An initial step in the method of recombinant production of the antigen involves the ligation of a DNA sequence encoding the antigen into a suitable expression vector containing a promoter and ribosome binding site operable in the host cell in which the coding sequence will be transformed. The most common examples of such expression vectors are plasmids which are double stranded DNA loops that replicate autonomously in the host cell. However, it will be understood that suitable vectors other than plasmids can be used in performing the invention.

Preferably, the host cell in which the DNA sequence encoding the peptide is cloned and expressed is a prokaryote such as E. coli. For example, E. coli DH5 (Raleigh E. A. et al Nucleic Acid Research 16 No 4 p 1563-1575 (1988), E. coli K12 strain 294 (ATCC 31446), E. coli B, E. coli X1766 (ATCC 31537) E. coli strain ST9 or E. coli JM 101 can be employed. Other prokaryotes can also be used, for example bacilli such as Bacillus subtilis and enterobacteriaceae such as Salmonella typhimurium, Serratia marcesans or the attenuated strain Bacille Calmette-Guerin (BCG) of Mycobacterium bovis.

In general, where the host cell is a prokaryote, expression or cloning vectors containing replication and control sequences which are derived from species compatible with the host cell are used. The vector may also carry marking sequences which are capable of providing phenotypic selection in transformed cells. For example, E. coli has commonly been transformed using pBR322, a plasmid derived from an E. coli species (Bolivar, et al., Gene 2: 95 (1977)). pBR322 contains genes for ampicillin and tetracycline resistance and thus provides easy means for identifying transformed cells.

For use in expression, the plasmid including the DNA to be expressed contains a promoter. Those promoters most commonly used in recombinant DNA construction for use with prokaryotic hosts include the β-lactamase (penicillinase) and lactose promoter systems (Chang et al, Nature, 275: 615 (1978); Itakura, et al, Science, 198: 1056 (1977); Goeddel, et al Nature 281: 544

(1979)) and a tryptophan (trp) promoter system (Goeddel, et al, *Nucleic Acids Res.*, 8: 4057 (1980); EPO Publ No. 0036776). While these are the most commonly used, other microbial promoters such as the tac promoter (Amann et al., *Gene* 25, 167–178 (1983)) have been constructed and utilised, and details concerning their nucleotide sequences have been published, enabling a skilled worker to ligate them functionally in operable relationship to genes in vectors (Siebenlist, et al, *Cell* 20: 269 (1980)).

In addition to prokaryotes, eukaryotic microbes, such as yeast may also be used. *Saccharomyces cerevisiae*, or common baker's yeast is the most commonly used among eukaryotic microorganisms, although a number of other strains are commonly available. For expression in Saccharomyces, the plasmid YRp7, for example, (Stinchcomb et al., *Nature* 282, 39 (1979); Kingsman et al., *Gene* 7, 141 (1979); Tschemper et al., *Gene* 10, 157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics* 85, 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073 (1980)) or other glycolytic enzymes (Hess et al., *J. Adv. Enzyme Reg.* 7: 149 (1968); Holland et al., *Biochemistry* 17 4900 (1978). Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequence is suitable.

In addition to microorganisms, cultures of cells derived from multicellular organisms such as mammals and insects may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture*, Academic Press, Kruse and Patterson, editors (1973)). Examples of such useful host cell lines are VERO and HeLa cells and Chinese hamster ovary (CHO) cells. Expression vectors for such cells ordinarily include (if necessary) an origin of replication, a promoter located upstream from the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus 2, and most frequently Simian Virus 40(SV40). The early and late promoters of SV40 virus are particularly useful because both are obtained easily from the virus as a fragment which also contains the SV40 viral origin of replication (Fiers et al., *Nature* 273, 113, (1978)). Smaller or larger SV40 fragments may also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV) source, or may be provided by the host cell chromosomal replication mechanism. If the vector is integrated into the host cell chromosome, the latter is often sufficient.

Upon transformation of the selected host with an appropriate vector, the antigenic peptide encoded can be produced often in the form of a fusion protein by culturing the host cells. The fusion protein is then recovered and purified as necessary.

Where the protein is produced in a soluble form, recovery and purification can be achieved using any of those procedures known in the art, for example by adsorption onto and elution from an anion exchange resin. As will be apparent from the specific examples provided, where the peptide of the invention is produced as a fusion protein, the carrier portion of the fusion protein can prove useful in this regard.

However, it has been the applicant's experience that only a minor proportion of the protein is expressed in a soluble form, with the major proportion being expressed in a non-soluble form contained with inclusion bodies within the transformed host. In such cases, a solubilisation technique can be employed to extract the product from the inclusion bodies and to render it soluble for subsequent processing and use.

Once again, any of those conventional techniques known in the art for this purpose can be employed. For a general review of these techniques, reference can be made to the following publications: Marston, F. A. O., "The purification of eukaryotic polypeptides synthesized in Escherichia coli"; *Biochem J* 240 1–12 (1986); and Sharma S. K., "On the recovery of Genetically Engineered Proteins from Escherichia coli", *Separation Science and Technology* 21 (8), pp 701–726 (1986). Of such techniques, urea solubilisation as described in Example 4 is preferred.

Following recovery of the antigenic peptide it is purified as desired. The purification procedure adopted will of course depend upon the degree of purity required for the use to which the peptide is to be put. For most vaccination purposes, separation of the fusion protein from most of the remaining components of the cell culture is sufficient as the antigen can be incorporated into a vaccine in a relatively crude form. However, in cases where a greater degree of purity is desired, the carrier component of the fusion protein can be cleaved from the antigenic component. As will again be apparent from the specific examples provided, this can be easily achieved through the provision of an appropriate enzyme cleavage site between the carrier component and the antigen.

Where as is preferred, recombinant techniques are used to produce the antigenic peptide, the first step is to obtain DNA encoding the desired product. Such DNA molecules comprises still a further aspect of this invention.

The DNA molecule of the invention preferably encodes the nucleotide sequence of FIG. 1. This DNA sequence can be obtained contained within a DNA molecule isolated from an appropriate natural source or can be produced as intron-free cDNA using conventional techniques such as those used in the specific description set out hereinafter.

However, as indicated above, the invention also contemplates variants of the peptide which differ from the native amino acid sequences by the insertion, substitution or deletion of one or more amino acids. Where such a variant is desired, the nucleotide sequence of the native DNA molecule is altered appropriately. This alteration can be made through elective synthesis of the DNA using an appropriate synthesizer such as the Applied Biosystems DNA Synthesizer or by modification of the native DNA by, for example, site specific or cassette mutagenesis.

Once obtained, the DNA molecule is treated to be suitable for insertion together with the selected control sequence into the appropriate cloning and/or expression vector. To this end the DNA is cleaved, tailored and religated as required.

Cleavage is performed by treating with restriction enzyme(s) in a suitable buffer. Any of the large number of commercially available restriction enzymes can be used as specified by the manufacturer. After cleavage, the nucleic acid is recovered by, for example, precipitation with ethanol.

Tailoring of the cleaved DNA is performed using conventional techniques. For example, if blunt ends are required, the DNA may be treated with DNA polymerase I (Klenow), phenol and chloroform extracted, and precipitated by ethanol.

Re-litation can be performed by providing approximately equimolar amounts of the desired components, appropriately tailored for correct matching, and treatment with an appropriate ligase (e.g. $T_4$ DNA ligase).

In addition to the protective stable antigens of the invention and the method of producing these, a further and most important aspect of the present invention relates to the use of the protective antigen as the active agent in a ruminant vaccine against *T.ovis* infection. In this aspect, the protective antigen of the invention can be administered either alone or in the form of a composition comprising the protective antigen of the invention as the active ingredient together with a pharmaceutically acceptable diluent carrier or adjuvant.

Examples of suitable adjuvants known to those skilled in the art are saponins (or derivative or related material), muramyl dipeptide, trehalose dimycollate, Freund's complete adjuvant, Freund's incomplete adjuvant, other water-in-oil emulsions, double emulsions, dextran, diethylaminoethyl-dextran, potassium alum, aluminum phosphate, aluminum hydroxide, bentonite, zymosan, polyelectrolytes, retinol, calcium phosphate, protamine, sarcosine, glycerol, sorbitol, propylene glycol, fixed oils and synthetic esters of higher fatty acids. Saponins have been found to be particularly effective adjuvants.

The protective antigen of the invention may also be treated in any conventional way to still further enhance its stability or to conserve or potentiate its immunogenic efficacy. For example, the antigen may be treated with a suitable inhibitor, modifier, crosslinker or denaturant in such a way as to enhance its immunogenicity.

In addition, the protective antigen can be administered in combination with other therapeutic agents such as anthelmintics, for example levamisole, or other vaccines.

The vaccine can be administered to the ruminant by any of those methods known in the art. However, the preferred mode of administration of the vaccine is parenteral. The term "parenteral" is used herein to mean intravenous, intramuscular, intradermal and subcutaneous injection. Most conveniently, the administration is by subcutaneous injection.

The amount of the vaccine administered to the ruminant to be treated will depend on the type, size and body weight of the ruminant as well as on the immunogenicity of the vaccine preparation. Conveniently, the vaccine is formulated such that relatively small dosages of vaccine (1 to 5 ml) are sufficient to protect the ruminant.

The immunogenicity of the antigenic peptide of the invention and its effectiveness as the active agent of a ruminant vaccine will be appreciated from the immunogenicity trials detailed in the Examples 4 and 5.

Specific non-limiting examples of the invention will now be described.

EXAMPLE 1

Identification and initial cloning of the stable antigen of the invention cDNA encoding the 45 W antigen is contained in *E. coli* 45 W which has been deposited at the American Type Culture Collection, Rockville, Md. 20852, USA under accession number 67505. The details of derivation of E. coli 45 W are fully set out in U.S. Ser. No. 07/349,723.

The entire 45 W complementary cDNA was cloned into the Eco RI site of the vector pUC18 (Yanisch-Perron *Gene* 33, 103–119 (1985)) prior to cloning into the plasmid pGEX-2T (Smith D. B. and Johnson, K. S. Gene 67, 31–40 (1988)). This plasmid pUC18-45W was digested with the restriction endonucleases *Bam* HI and Xho II. The DNA was electrophoresed on agarose gels and the *Bam HI/Xho* II fragment containing 45 W DNA was purified. This fragment was then ligated with pGEX-2T DNA digested with *Bam* HI and transformed into the *E. coli* strain JM101 (Yanisch-Perron *et al.*, 1985 supra).

The appropriate clones were selected on the basis of their DNA insert size and molecular weight of their affinity purified GST fusion proteins (Smith and Johnson Gene (1988) supra). The approximate molecular weight of the *T.ovis* portion of the pGEX-2T-45W (*Bam* HI/*Xho* II) fusion protein is 23841, calculated from the DNA sequence of the molecule. This fusion protein when electrophoresed on a 13% SDS gel and stained with Coomassie blue was found to be stable.

The *T.ovis* portion of the 45 W DNA sequence contained in the clone pGEX-2T-45W (*Bam* HI/*Xho* II) is set out in FIG. 1. The predicted amino acid sequence for this *T.ovis* antigen fragment is also set out in this Figure.

It will however be appreciated that the non-GST portion of cloned fusion protein GST 45W(B/X) includes a small number of additional amino acids in addition to those encoding the fragment of the *T.ovis* polypeptide. These additional amino acids are included as a consequence of the cloning and expression of the *T.ovis* fragment as described above.

The non-GST portion of the fusion protein is hereinafter called "45W(B/X)".

EXAMPLE 2

Demonstration of antigenicity of the GST-45W(B/X) fusion protein

Western blot analysis was performed with the fusion proteins prepared as described in U.S. Ser. No. 07/349,723 from pGEX-2T-45W (Bam HI/Xho II), pSj10ΔBam7Stop7-45S and pGEX-2T-45W. These fusion proteins were electrophoresed on SDS-polyacrylamide gels, transferred to nitrocellulose and probed with the 45 W specific monoclonal antibody 3F10F6 prior to incubation with $^{125}$I-labeled protein A.

Antibody 3F10F6 was prepared as follows;

BALB/c mice were immunised with GST 45 W fusion protein and hybridomas were prepared according to the method of Fazekas de St. Groth and Scheidegger (*J. Immunological Methods* 35 1–21, Production of Monoclonal Antibodies; Strategy and tactics (1980)). Monoclonal antibody 3F10F6 was selected by ELISA analysis of hybridoma supernatants against GST 45 W, and was purified by the method of Reik et al (1987, *J. Immunological Methods* 100, 123–130).

The results are shown in FIG. 2. As can be seen by reference to this Figure, a positive reaction was obtained with antibody 3F10F6 in relation to the antigen expressed by host cells transformed with pGEX-2T-45W (Bam HI/Xho II). This indicated that the stable peptide was likely to be immunogenic.

EXAMPLE 3

Preparation of fusion protein for immunogenicity trials

An equivalent procedure to that set out in Example 1 was adopted to prepare fusion protein for the immunogenicity trials. The host cell chosen to express the fusion protein was in this case *E. coli* DH5 transformed as follows.

The entire 45 W cDNA was cloned into the Eco RI site of the vector pUC 18 (Yanisch-Perron, Gene 33, 103–119, 1985) prior to cloning into the plasmid pGEX-2T (Smith and Johnson, *Gene* (1988) supra). This plasmid pUC 18 was digested with the restriction endonucleases Bam HI and Xho II. The DNA was electrophoresed on agarose gels and the Bam HI/Xho II (658 bp) fragments containing 45 W DNA were purified. These fragments were then ligated with pGEX-2T DNA digested with Bam HI and transformed into the *E. coli* strain DH5.

An overnight 100 ml culture of transformed *E. coli* DH5 was added to a shaker flask containing 800 ml SOB medium containing 0.1 mg/ml ampicilin. After 30 minutes, fusion protein expression was induced by adding IPTG to 0.021 mg/ml and culturing continued for a further 6 hours. The bacteria were pelleted by centrifugation at 5000×g for 30 minutes and the cell pellet (net weight=4.7 g) was resuspended in 22 ml PBS pH7.4. Lysozyme and triton-X-100 were added to 0.25 mg/ml and 0.5% final concentration respectively and the suspension was mixed for 10 minutes at ambient temperature. The bacteria were disrupted by sonication and the lysate was centrifuged at 4500×6 for 40 minutes. Soluble fusion protein GST-45W(B/X) was purified from the supernatant by affinity chromatography as follows.

The supernatant was mixed at room temperature with 50 ml washed glutathione-agarose beads (sulphur linkage, Sigma) for 30 minutes. After absorption, the unbound supernatant was eluted and the beads washed on a sintered glass filter with 5×200 ml volumes of PBS. Fusion protein was eluted in 2×25 ml volumes (5 minutes each volume) of 50 mM Tris-HCl pH 8.0 containing 5 mM reduced glutathione (Sigma) freshly prepared.

To solubilise the non-soluble fusion protein, the pellet was resuspended in 15 ml of 50 mM borate buffer pH 9.0 containing 2 mM EDTA and 1 mM DTT. A 5 ml aliquot was removed and stored frozen at −18° C. The remaining 10 ml suspension was made up to 25 ml by addition of borate buffer and dry urea to a final concentration of 7.0 M and was mixed for 2 days at ambient temperature. Triton X-100 was added to 0.4% final concentration and the solution was dialysed initially against borate buffer as above followed by PBS pH 7.2 over 3 days. The dialysed protein solution was centrifuged at 35000×g for 30 minutes at 4° C. and the clear supernatant retained.

Part of the urea solubilised pellet was kept for vaccination trials and part was further processed by affinity chromatography on glutathione-agarose as described previously. Amount of fusion protein recovered at each step is shown in Table 1. The proportion of fusion protein GST 45W(B/X) relative to E.coli protein was calculated by densitometry of Coomassie Blue stained SDS-PAGE gels (Andrews A. T., 1986, Electrophoresis, Oxford University Press).

TABLE 1

| Amount of GST 45W(B/X) recovered during processing | | | |
|---|---|---|---|
| | Total Protein | % Fusion Protein | Fusion Protein |
| soluble affinity purified | 8.5 mg | 80 | 6.8 mg |
| urea solubilised pellet | 42.5 mg | 37 | 15.7 mg |
| urea solubilised, affinity purified | 3.0 mg | 71 | 2.1 mg |

EXAMPLE 4

Vaccination trials with fusion protein extracts

In an initial experiment 5 Romney sheep aged 10 months were immunised with 2 subcutaneous injections of 5 ug of GST 45W(B/X) plus 1 mg saponin in 1 ml saline, four weeks apart. A booster inoculation of 10 ug fusion protein plus saponin was given three weeks later, and the sheep were infected 4 weeks later with 1200 *T.ovis* eggs. Three control sheep were given injections of GST carrier protein in the same manner.

In a second experiment groups of sheep were immunised as follows:

| Group | Antigen | Total dose of fusion protein* | Adjuvant |
|---|---|---|---|
| 1 | Saline control | — | saponin, 1 mg |
| 2 | Affinity purified | 58 ug | " |
| 3 | Urea extract | 132 ug | " |
| 4 | Urea extract + affinity purified | 90 ug | " |

*given in three injections

Four weeks after the final immunisation all sheep were infected with 2400 *T.ovis* eggs.

Six weeks after infection sheep were humanely slaughtered and carcases examined for cysts.

Results are shown in Table 2.

TABLE 2

Protection data from vaccination trials

| Group | Antigen | Number of cysts* | Mean | % Reduction |
|---|---|---|---|---|
| Trial A | | | | |
| 1 | GST | 15 28 63 | 35.3 | — |
| 2 | GST 45W(B/X) affinity purified | 0 0 0 0 20 | 4.0 | 89 |
| Trial B | | | | |
| 1 | Saline | 3 12 14 15 16 17 40 | 16.7 | — |
| 2 | GST 45W(B/X) affinity purified | 0 0 0 0 1 | 0.2 | 99 |
| 3 | Urea extract | 0 0 0 1 | 0.25 | 98 |
| 4 | Urea extract + affinity purified | 0 0 0 2 | 0.5 | 97 |

*Trial A: numbers of cysts in whole carcase
Trial B: numbers of cysts in masseters, heart, diaphragm and external carcase.

It can therefore be seen that immunisation with the fusion protein GST-45W(B/X) resulted in a highly significant reduction in cyst numbers compared with the controls used.

EXAMPLE 5

Antibody response of sheep immunised with GST 45W(B/X)

Sera from sheep immunised with the extracts described above were analysed by immunoblotting and ELISA.

Immunoblotting was performed as described by Johnson et al Nature (1989) supra)) and showed that sheep immunised with the fusion protein GST 45W(B/X) made antibodies which recognised oncosphere antigens with relative mobilities of 47-52000 as described for antibody responses to the parent antigen GST 45W (Johnson et al., Nature 1989, supra). These results are shown in FIG. 3.

The GST portion of GST 45W(B/X) was removed by thrombin cleavage and the 45W(B/X) protein obtained free from GST by depletion on glutathione-agarose as described (Smith and Johnson Gene 1988, supra). The 45W(B/X) protein was used as antigen to coat microtitre plates for a standard ELISA as described in "Practice and Theory of Enzyme Immunoassays", P. Tijssen, Laboratory Techniques in Biochemistry and Molecular Biology; Volume 15, Elsevier Science Publishers (1985).

Sheep antibody was detected with peroxidase-conjugated rabbit anti-sheep lgG (Cappel, Cooper Biomedical Inc.).

The results are shown in FIG. 4. As can be seen from this Figure, immunisation of sheep with affinity purified fusion protein or urea extracted fusion protein stimulated strong antibody responses in all groups of sheep.

In accordance with the present invention there is provided a stable peptide comprising a fragment of a T.ovis polypeptide which is effective in generating a protective immunological response against T.ovis infection in ruminants. It has been established that vaccination with this peptide stimulates almost complete immunity against challenge infection with T.ovis eggs. Insofar as the applicants are aware, it is the highest level of protection thus far achieved in a natural host-parasite system by injection of a single antigen. The invention also provides a recombinant method for expression of the antigen by which commercial quantities can be obtained.

It will be appreciated that the above description is provided by way of example only and that variations in both the materials and the techniques used which are known to those persons skilled in the art are contemplated.

We claim:

1. A stable antigenic immunologically active protective peptide essentially free from naturally occurring admixtures, said peptide comprising a fragment of a T. ovis oncosphere antigen which runs as a 47-52 kDa doublet on SDS-PAGE, which fragment:
   (a) has a molecular weight of from about 23 kDa to about 24 kDa; and
   (b) generates a protective immunological response to T. ovis infection in a ruminant;
   or a stable protective subfragment of said 23-24 kDa fragment which subfragment generates a protective immunological response to T. ovis infection.

2. A peptide as claimed in claim 1, comprising the amino acid sequence:

| 1 | | CG | GAC Asp | TAC Tyr | GAA Glu | CAA Gln | CCC Pro | ATC Ile | GAG Glu | AGA Arg | ACA Thr | GTG Val | GTA Val | GAA Glu | 12 |
|---|---|---|---|---|---|---|---|---|---|---|---|---|---|---|---|
| 39 | TAT Tyr | CCA Pro | TCA Ser | CTA Leu | CGT Arg | GAC Asp | ATC Ile | TTT Phe | GCT Ala | TGG Trp | GAA Glu | CCT Pro | CCG Pro | ACT Thr | TCT Ser | 27 |
| 84 | AAC Asn | TCC Ser | ATT Ile | GGC Gly | CTA Leu | ACT Thr | TGG Trp | CAA Gln | AGG Arg | CAT His | GCA Ala | TTT Phe | CCT Pro | GGT Gly | GTG Val | 42 |
| 129 | GAA Glu | CGT Arg | GAA Glu | GTG Val | CTC Leu | ACA Thr | TTG Leu | AAG Lys | GCA Ala | GTG Val | CCG Pro | ACT Thr | TCT Ser | GAA Glu | CCC Pro | 57 |
| 174 | AAT Asn | AAC Asn | ACC Thr | AAG Lys | ACA Thr | GCA Ala | TAT Tyr | GCA Ala | AAG Lys | CTC Leu | GGC Gly | AGC Ser | GGA Gly | AAA Lys | GTC Val | 72 |
| 219 | ACT Thr | CTT Leu | GAT Asp | GGA Gly | CTG Leu | AAG Lys | CCC Pro | AAT Asn | GCC Ala | ACA Thr | TAT Tyr | CTT Leu | GTG Val | ACT Thr | GCG Ala | 87 |
| 264 | ACG Thr | GCA Ala | AAT Asn | ATA Ile | AGT Ser | GGA Gly | GAC Asp | ACA Thr | ATT Ile | CTG Leu | GTA Val | TTG Leu | AGC Ser | AAT Asn | ACT Thr | 102 |
| 309 | TTT Phe | CAT His | ACA Thr | CTG Leu | GCC Ala | AAT Asn | GGC Gly | ACA Thr | AAT Asn | ATT Ile | ATA Ile | AAT Asn | AAC Asn | ATC Ile | TTC Phe | 117 |
| 354 | CAT His | TGG Trp | GGT Gly | CCT Pro | GTG Val | ACT Thr | AAT Asn | CAA Gln | TCA Ser | ATT Ile | CAA Gln | GTA Val | AGA Arg | TGG Trp | GAT Asp | 132 |

-continued

| | | | | | | | | | | | | | | | | |
|---|---|---|---|---|---|---|---|---|---|---|---|---|---|---|---|---|
| 399 | CAG | ATA | AAA | CCG | GAG | GAA | ACA | AGC | GCT | CTG | ATA | GTC | ACA | CTG | ACG | |
| | Gln | Ile | Lys | Pro | Glu | Glu | Thr | Ser | Ala | Leu | Ile | Val | Thr | Leu | Thr | 147 |
| 444 | GCA | GAG | ATG | GCT | TCT | GAC | CCC | GGA | GTG | GAA | AGA | TCG | GAG | TCT | GCA | |
| | Ala | Glu | Met | Ala | Ser | Asp | Pro | Gly | Val | Glu | Arg | Ser | Glu | Ser | Ala | 162 |
| 489 | CTC | TTC | GGT | AAA | GGA | AAC | GTC | ACT | GTT | GAC | GGA | CTG | GAG | TCC | GAC | |
| | Leu | Phe | Gly | Lys | Gly | Lys | Val | Thr | Val | Asp | Gly | Leu | Glu | Ser | Asp | 177 |
| 534 | ACA | CTA | TAT | ATT | GCG | ACT | GTG | ATG | GTA | TTT | AGA | AAT | GGA | AGG | CAA | |
| | Thr | Leu | Try | Ile | Ala | Thr | Val | Met | Val | Phe | Arg | Asn | Gly | Arg | Gln | 192 |
| 579 | TAC | TTC | AAT | TCC | ACC | AGA | GAT | ATT | CGA | ACA | CTC | AAA | TCT | GGC | CAT | |
| | Tyr | Phe | Asn | Ser | Thr | Arg | Asp | Ile | Arg | Thr | Leu | Lys | Ser | Gly | His | 207 |
| 624 | AAG | GAG | GTA | ACA | GTC | GTA | ACA | ACT | AGT | GGA | TC | | | | | |
| | Lys | Glu | Val | Thr | Val | Val | Thr | Thr | Ser | Gly | | | | | | | or a protective subfragment thereof, which subfragment generates a protective immunological response to *T. ovis* infection.

3. A peptide as claimed in claim 1 which is the product of expression of a nucleotide sequence coding therefor in a host cell.

4. A peptide as claimed in claim 3 which is expressed in the host cell as a fusion protein.

5. A peptide as claimed in claim 4 which is expressed as a fusion protein with the enzyme glutathione s-transferase.

6. A composition capable of generating a protective immunological response to T. ovis infection in a ruminant, said composition consisting essentially of a pharmaceutically acceptable adjuvant, carrier or diluent a component selected from the group consisting of:
(a) a protective peptide as claimed in claim 2,
(b) a stable immunologically active protective subfragment of a peptide as claimed in claim 2.

7. An isolated and essentially purified DNA molecule comprising a nucleotide sequence which encodes a purified stable protective antigenic peptide comprising a fragment of a *T. ovis* polypeptide antigen which runs as a 47–52 kDa doublet on SDS-PAGE which fragment:
(a) has a molecular weight of from about 23 kDa to about 24 kDa;
(b) generates a protective immunological response to *T. ovis* infection in a ruminant; or
which encodes a protective subfragment, said subfragment generating a protective immunological response to *T. ovis* infection.

8. An isolated and essentially purified DNA molecule which encodes an immunologically active protective peptide comprising a fragment of a *T. ovis* polypeptide which fragment is coded for by the nucleotide sequence 9. An isolated and essentially purified DNA molecule selected from the group consisting of:
(a) a nucleotide sequence encoding an immunologically active protective peptide as claimed in claim 2;
(b) a nucleotide sequence encoding a stable immunologically active protective subfragment of a peptide as claimed in claim 2.

10. An isolated and essentially purified DNA molecule comprising a 655 bp fragment of DNA as shown in FIG. 1 contained within *E. coli* transformant 45 W (ATCC accession number 67507) encoding a stable immunologically active protective peptide comprising a fragment of a polypeptide of *T. ovis*.

11. A DNA molecule as claimed in claim 7 which has been isolated from a natural source.

12. A DNA molecule as claimed in claim 7 which is intron-free.

13. A recombinant expression vector which contains a DNA molecule as claimed in claim 7.

14. A vector pGEX-2T-45W, consisting essentially of the Bam HI to Xho II fragment of *T. ovis* DNA as shown in FIG. 1.

15. A host cell transformed with a vector as claimed in claim 13 and capable of expressing the *T. ovis* peptide or fragment thereof which is encoded.

16. A host cell as claimed in claim 15 which is a prokaryote.

17. A host cell as claimed in claim 16, wherein the prokaryote host is *E. coli*.

18. A host cell as claimed in claim 17, wherein the prokaryote host is *E. coli* DH5.

19. A host cell as claimed in claim 15, which is a eukaryote.

20. A method of producing a stable antigenic immunologically active protective peptide essentially free from naturally occurring admixtures, said peptide comprising a fragment of a *T. ovis* oncosphere antigen which

| | | | | | | |
|---|---|---|---|---|---|---|
| 1 | CGG | ACTACGAACA | ACCCATCGAG | AGAACAGTGG | TAGAATATCC | ATCACTACGT |
| 54 | GACATCTTTG | CTTGGGAACC | TCCGACTTCT | AACTCCATTG | GCCTAACTTG | GCAAAGGCAT |
| 114 | GCATTTCCTG | GTGTGGAACG | TGAAGTGCTC | ACATTGAAGG | CAGTGCCGAC | TTCTGAACCC |
| 174 | AATAACACCA | AGACACATA | TGCAAAGCTC | GGCAGCGGAA | AAGTCACTCT | TGATGGACTG |
| 234 | AAGCCCAATG | CCACATATCT | TGTGACTGCG | ACGGCAAATA | TAAGTGGAGA | CACAATTCTG |
| 294 | GTATTGAGCA | ATACTTTTCA | TACACTGGCC | AATGGCACAA | ATATTATAAA | TAACATCTTC |
| 354 | CATTGGGGTC | CTGTGACTAA | TCAATCAATT | CAAGTAAGAT | GGGATCAGAT | AAAACCGGAG |
| 414 | GAAACAAGCG | CTCTGATAGT | CACACTGACG | GCAGAGATGG | CTTCTGACCC | CGGAGTGGAA |
| 474 | AGATCGGAGT | CTGCACTCTT | CGGTAAAGGA | AAGGTCACTG | TTGACGGACT | GGAGTCCGAC |
| 534 | ACACTATATA | TTGCGACTGT | GATGGTATTT | AGAAATGGAA | GGCAATACTT | CAATTCCACC |
| 594 | AGAGATATTC | GAACACTCAA | ATCTGGCCAT | AAGGAGGTAA | CAGTCGTAAC | AACTAGTGGA |
| 654 | TC | | | | | | runs as a 47-52 kDa doublet on SDS-PAGE, which fragment has a molecular weight of from about 23 kDa to about 24 kDa and which generates a protective immunological response to *T. ovis* infection in a ruminant, or a stable protective subfragment of said 23-24 kDa fragment which subfragment generates a protective immunological response to *T. ovis* infection, said method comprising the steps of:

culturing a cell as claimed in claim 15, and
recovering the expressed peptide.

21. A method as claimed in claim 20, wherein the antigenic peptide is recovered in a soluble form.

22. A method as claimed in claim 20, wherein the antigenic peptide is recovered in an insoluble form and is subsequently solubilized.

23. A stable antigenic peptide comprising a fragment of the *T. ovis* polypeptide antigen which runs as a 47-52 kDa doublet on SDS-PAGE produced by the method of claim 20.

24. A vaccine comprising an immunologically-effective amount of a stable immunologically active protective peptide as claimed in claim 1 in combination with a pharmaceutically acceptable adjuvant, carrier or diluent therefor.

25. A method of protecting a ruminant against *T. ovis* infection, which method comprises the step of administering to a said ruminant a stable immunologically active protective peptide as claimed in claim 1 in an amount effective to generate in said ruminant a protective immunological response to *T. ovis* infection.

26. A method of protecting a ruminant against T. ovis infection, which method comprises the step of administering to a said ruminant a composition as claimed in claim 6 in an amount effective to generate in said ruminant a protective immunological response to *T. ovis* infection.

27. A method of protecting a ruminant against T. ovis infection, which method comprises the step of administering to a said ruminant a vaccine as claimed in claim 24 in an amount effective to generate in said ruminant a protective immunological response to *T. ovis* infection.

* * * * *